United States Patent [19]

Hope

[11] Patent Number: 5,083,452
[45] Date of Patent: Jan. 28, 1992

[54] METHOD FOR RECORDING MULTI-PHASE FLOWS THROUGH A TRANSPORT SYSTEM

[75] Inventor: Bjorn R. Hope, Lommedalen, Norway

[73] Assignee: Sensorteknikk A/S, Lommedalen, Norway

[21] Appl. No.: 476,464

[22] PCT Filed: Dec. 16, 1988

[86] PCT No.: PCT/NO88/00096
§ 371 Date: Jun. 5, 1990
§ 102(e) Date: Jun. 5, 1990

[87] PCT Pub. No.: WO89/05974
PCT Pub. Date: Jun. 29, 1989

[30] Foreign Application Priority Data
Dec. 18, 1987 [NO] Norway ................. 875326

[51] Int. Cl.$^5$ ............... G01N 11/00; G01F 1/00
[52] U.S. Cl. ..................... 73/61 R; 73/861.21
[58] Field of Search ........... 73/19.03, 61.1 R, 61 R, 73/861.04, 861.18, 861.21, 861.22, 861.24

[56] References Cited

U.S. PATENT DOCUMENTS

| | | | |
|---|---|---|---|
| 4,019,384 | 4/1977 | Herzl | 73/861.24 |
| 4,339,661 | 7/1982 | Pitt et al. | 73/861.22 |
| 4,587,849 | 5/1986 | Gross | 73/644 |
| 4,639,593 | 1/1987 | Stetson et al. | 73/861.21 |
| 4,674,337 | 6/1987 | Jonas | 73/861.21 |
| 4,836,032 | 6/1989 | Redus et al. | 73/861.04 |
| 4,856,344 | 8/1989 | Hunt | 73/861.04 |

Primary Examiner—Robert Raevis
Assistant Examiner—Shu-Cheng Kau
Attorney, Agent, or Firm—Rodman & Rodman

[57] ABSTRACT

A method for determining the flow situation in a transport system where the flow medium occurs in multi-phase and is conducted through a structural detail such as a choke valve, which acts on the flow of the medium and produces turbulence causing acoustic energy signals which are generated in and immediately close to the structural detail. The acoustic energy signals are sensed by one or a plurality of acoustic sensors with an acoustic broad-band connection with the structural detail. The sensor converts the energy signal to transmittable signals to a signal processing unit utilizing known signal analysis principles to provide interpretable information on the actual flow situation and the flowing medium which is influenced by the structural detail. The structural detail to which the acoustic sensor is connected may be incorporated in a subsea production system.

16 Claims, 8 Drawing Sheets

METHOD FOR RECORDING MULTI-PHASE FLOWS THROUGH A TRANSPORT SYSTEM

The present invention relates to a method for determining the composition and flow condition of a medium flowing through a structural detail influencing the flow. Acoustic signals generated from the medium flowing through said structural detail are collected at the surface of the latter. By structural detail is meant a device through which a medium is flowing. It may be a valve, a duct, or a pipe, or a choke mechanism which is shaped to provide strong turbulence/cavitation in the medium or part of the medium.

In connection with monitoring multiphase production flow as for example, in oil wells when it is desirable to control production rate, i.e. the ratio of oil/gas, and in the production of water, and when monitoring production in cases with resulting sand production, continuous monitoring of the production parameters may be of great importance.

In installations comprising special structural details which control the production process by direct mechanical influence on the flow conditions, e.g. various kinds of choke devices for pressure control, state monitoring of said devices will be important, especially if they are difficult to access, e.g. in connection with sub sea installations and in case of unmanned remote controlled plants. Due to the fact that changes of the structural turbulence/cavitation causing details are represented in the detected acoustic spectrum of signals, it will be possible to record mechanical changes (e.g. wear, changes of the choking ratio, any possible deposits).

There are various known methods and devices for monitoring fluctuations of flow, mainly based on various kinds of methods for detecting fluctuations of pressure in a pipe system with turbulent flow. In this connection we refer to DE-AS Nos. 14 73 019 and 14 98 271, as well as to NO-PS No. 141 327. An unfavourable aspect of said known systems is that physical intervention in the pipe system is required to gauge the pressure.

U.S. Pat. No. 4,392,374 discloses a device for sensing inhomogeneities, e.g. gas bubbles, in liquid flow guided in a pipeline. An electromechanical detector means is attached to the outside of the pipe to provide acoustic connection. The device is designed to constitute a band pass filter excluding undesired vibration frequencies. It is, among others, disadvantageous in said known concept that essential information signals are lost due to filtration, and that the detector is quite dependent on firm clamping on the pipe.

In NO-PS No. 140 838 a monitoring device for solids, e.g. sand, in a fluid flow through a pipeline is disclosed. The device is acoustically connected with the pipeline, via a liquid filled space, and is placed at a pipe bend. Due to inertia relative to the fluid some of the grains of sand may move along the pipe wall which may result in acoustic signals. Such slight impingements will be acoustically recorded by the detector means. In case of a pure fluid or a fluid, e.g. comprising air and water, there will be approximately zero reaction from the detector. If the pipeline carries gas containing a condensate precipitations may be caused to form on the inside of the pipe and there is, thus, a hazard of a considerably reduced detection efficiency when the fluid contains grains of sand later on.

According to the invention known disadvantages and deficiencies of the known devices are avoided due to the fact that turbulence/cavitation is created in the medium passing through, by the aid of the structural detail. Acoustic energy signals are thus generated and propagate in the structure, and the acoustic energy signals are transformed by the aid of acoustic sensor means having an acoustic connection with the structural detail, into transmittable signals which are processed by the aid of relevant analytical methods in order to provide interpretable information on the composition and flowing conditions of the passing medium.

A method is, thus, provided by the invention which by the aid of simple means permits scanning and recording of acoustic signals generated by turbulence and cavitation, without the sensor being exposed to the medium. In principle, this means that any mechanical adaption of the structure is avoided, and that the sensor may readily be provided on existing installations. Replacement and calibration of the sensor is also easy. The choice of the kind of sensor to be used is mainly dependent on the amount and kind of information which one desires to derive from the source of signals. Due to the fact that the flow is influenced in greater or less degree by the structure, the content of information in the signal spectrum will also vary. For instance, a sensor system which is sensitive to acceleration (accelerometer) across a sufficient bandwidth will be a suitable sensor system which is able to pick up a wide range of signal details. In cases with signal information in a frequency range from 50 kHz and up into the range of MHz, the limit is reached of the range of sensitivity and frequency of the accelerometer. Then, obviously, a velocity sensing system of a known design may be used, e.g. by the aid of a piezoelectric signal transformer transforming acoustic waves on the surface of the structure into electric signals.

Velocity sensors are commonly a more simple kind of sensors which are able to transform sufficient signal information, in lower frequency ranges as well. The choice of sensor is greatly determined by the desired detailed information on flow conditions, and by the composition of the measured medium. There are great differences in signal composition. Signals generated by a medium containing much gas, e.g. show a completely different composition in the frequency spectrum from the signal from liquid flows.

Flow parameters in a transport system may, thus be determined, since liquids, gases and particles are forced into a turbulent/cavitating state due to the structural design, and this will cause acoustic energy signals which are recordable on the surface of the structural detail. With a suitable design of the structure, i.e. occurrence of cavitation, the acoustic energy will comprise sufficient information to permit determination of the flow parameters of the passing medium as regards liquids, gases, particles, the ratio of gases/liquids and the mutual distribution of the latter, in certain cases occurring as liquid/gas pockets, so-called slug formation.

The acoustic signal is generated in and closely to the structural detail and is recorded by one or a number of acoustic sensor means which are suitably arranged on the structure, and with good acoustic coupling with the structural detail. Under certain conditions it may be suitable to use a sensor system with associated signal transmission. An acoustic sensor with both the sensor and the signal transmission being based on fibre-optic principles will be suitable in connection with installations in explosive areas, and possibly, with subsea installations where systems that are based on electric signals might be unsuitable. The acoustic signal is transformed into a transmittable signal to a signal processing unit utilizing signal analysis principles known per se to provide interpretable information on the actual flow situation in the structural detail.

A frequency analysis of the actual signal may yield a spectral division of the signal in the frequency level which comprises detailed information for recording the flow parameters of the passing medium, as well as changes of the structure due to influence from the medium passing through, as well as due to other influence.

By the present method flow velocity is, thus, recorded of liquid/gas, as well as of any particles through a transport system where the flow is forced into a highly turbulent state with cavitation by the aid of a mechanical structural detail having direct contact with the flowing medium. In this manner a complex acoustic signal is generated and propagates via the structure. Such measuring is especially important to enable recording of changes of the phases of the passing medium, i.e. the ratio of different liquids, liquids and gases, so called slug formation, particles, pressure and temperature states, and changes of a constricted area through which the flowing medium is passing. Changes of the ratio of constriction may be a result of a mechanical adjustment and/or a gradual effect that may be caused by erosion, cavitation, or other effects of wear.

A special variant is obtained when changes of flow are caused by precipitation on the inside of a pipeline system, and when the consequently generated acoustic signal is used to record changed flow conditions. An example occurs in connection with gas production. Due to temperature drop in the transport system hydrate formations occur which, in turn, affect flow conditions by precipitating on the inside of the pipe. As a result, signals are generated which may be picked up outside the transport system. Suitably arranged sensors permit localization of the source of signals.

The signal is sensed by the aid of a suitable signal converter being coupled (acoustically, via liquid, or the like) with the surface of the structure, and which, thus, permits flow parameters to be recorded without direct mechanical contact with the measured medium, and without intrusion into the structure. This results in a highly simplified service and, possibly, replacement procedures. Direct contact with the measured medium is most unfortunate due to various forms of erosion, especially flows of particles which would soon affect the sensor parameters and cause destruction. This is completely avoided by the present invention. According to the invention the acoustic sensor means is acoustically coupled to the structural detail which is in direct contact with the flowing medium, and from which the acoustic signal is derived directly or indirectly. Such a structural detail may be a choke valve through which a multi-phase medium flows. The medium is, thus, forced into strong turbulence/cavitation in the choking mechanism of the valve, causing generation of strong and complex acoustic signals which are a result of the actual flow condition.

The design of the choking mechanism will greatly influence the relation between the information contained in the acoustic signal and the actual flow condition as regards the composition of the flowing medium, and whether the flow is homogeneous, i.e. formation of liquid/gas pockets (slug formation). In cases of occurring cavitation different liquid fractions will show characteristic sound images due to the fact that different vapour pressure of the liquid will produce acoustic signals as a result of implosions occurring after a pressure increase following a drop in the pressure in the area of cavitation. If only a relatively weak turbulence or increase of the same occurs by the aid of the structural detail, the content of the signal will, obviously, be correspondingly reduced.

By the aid of methods known per se for signal analysis, it will be possible to find the relation between the acoustic signal image and the actual flow situation as regards the different variables which are included and which partly may be read directly from the signal, and partly by the aid of empirical methods. On that basis the flow condition can be determined.

Utilization of the invention in connection with a subsea production system may, e.g. permit control of important well parameters, both for an optimalized production, and for supervision of important process details, as flow like conditions, composition of the flowing medium, sand production, changes of pressure and temperature, any hydrate formation, leaks, wear, and the position of flow valves.

The recorded signal is composed of a large number of frequencies showing great difference of mutual strength. In the signal processing unit various forms of signal analysis will take place, which mainly divide the signal into narrow frequency bands (spectrum), e.g. by the aid of a FFT-analysis or some other kind of filtration technique.

Dependent on the turbulence/cavitation producing design of the structure the spectral distribution of various frequency components of the signal will indicate flow conditions as mentioned above. Certain phenomena will appear clearly from one single frequency spectrum, whereas others result from extensive methods of analysis and calculation. Certain dominant phenomena may, for instance, be explained on the basis of the signal level within a characteristic frequency range. In other cases the signal is so complex that, in addition to common frequency analysis, extensive analysis techniques of methods known per se will be required, which also comprise various forms of correlation analysis, and mathematical statistical calculations, to arrive at the desired parameters.

In recording, e.g. flow parameters in a structure designed as a control valve in an oil well, the acoustic signals are picked up on the surface of the valve by the aid of broadband accelerometers. The primary function of said valve is to control the well by the aid of a choke mechanism which, in turn, acts as an efficient turbulence/cavitation causing detail and a good source of signals with a detailed content of the composition of the medium passing through.

The medium passing through said valve with a relatively high pressure and temperature, may have quite different compositions of oil, gas, water, and sand. Gas which is not dissolved in liquid often occurs in the shape of gas pockets, so called slugs. Said phenomena will cause a complex signal image in both time and frequency aspects. Additionally, there are variables in the shape of choke opening, geometry, and long-time effects of erosion and cavitation. The information is mainly distributed in a spectrum with low frequency phenomena occurring in the low frequency signal range, e.g. slug formation, as opposed to liberation of gas from various liquids causing high frequency components.

Said example represents a complicated composition of many variables and will, thus, require relatively complex signal analysis, based on various utilizations of signal analysis methods known per se. Certain parameters are so characteristic that they may, e.g. be explained by the aid of simple frequency analyses, whereas others are so complex spectrally that various forms of sophisticated signal analysis will be required.

As regards, e.g. the power spectrum of the signal over a certain time interval, it may also be divided in the frequency range in a large number of variables. The latter are included in a multi-variable regression analysis with known measurable quantities of the flowing medium which passed through the valve during a known period of time. By carrying out a number of subsequent tests under different conditions we can construct a calibration model which will explain the composition of the passing well flow, and the variables being directly connected with mechanical conditions in the valve, on the basis of the variation of content of the signal spectrum.

The method in connection with the above stated for determining how the interrelationship between the acoustic signal and actual flow conditions is related to individual variables, is in many cases based on a combination of a signal analysis and mathematical statistical data processing. Multi-variable regression Partial Least Squares, may advantageously be used to establish a quantitative model between the spectral variables, designated X, and known variables, in this case designated Y. Traditional regression terminology is used, with the Y variable called the dependent variable, and X variables called independent variables. The relation of the Y variables with X variables forms the regression model. After calculation of this model, new X data may be used to predict associated Y-data.

Regression/prediction comprises two phases:

1. Calculation of the parameters of the regression model, based on associated sets of X and Y data, a sort of calibration or learning phase.

2. Determination of a new set of Y data from a set of new X data by introducing them into the calibration model.

Examples of systems utilized are signal analysis software from Signal Technology Inc. USA, and multivariable regression software, Unscrambler from CAMO, Norway.

Further characterizing features of the invention will appear from the following claims, as well as from the following disclosure with reference to the enclosed drawings.

For simplicity, the drawings show systems with only one sensor means used. Obviously, a plurality of sensors which are strategically placed on the structure will highly contribute to a more many-sided acoustic information picture. This is especially due to the fact that it will permit a higher degree of signal processing with correlation analysis between various sensor means.

Figure 1:
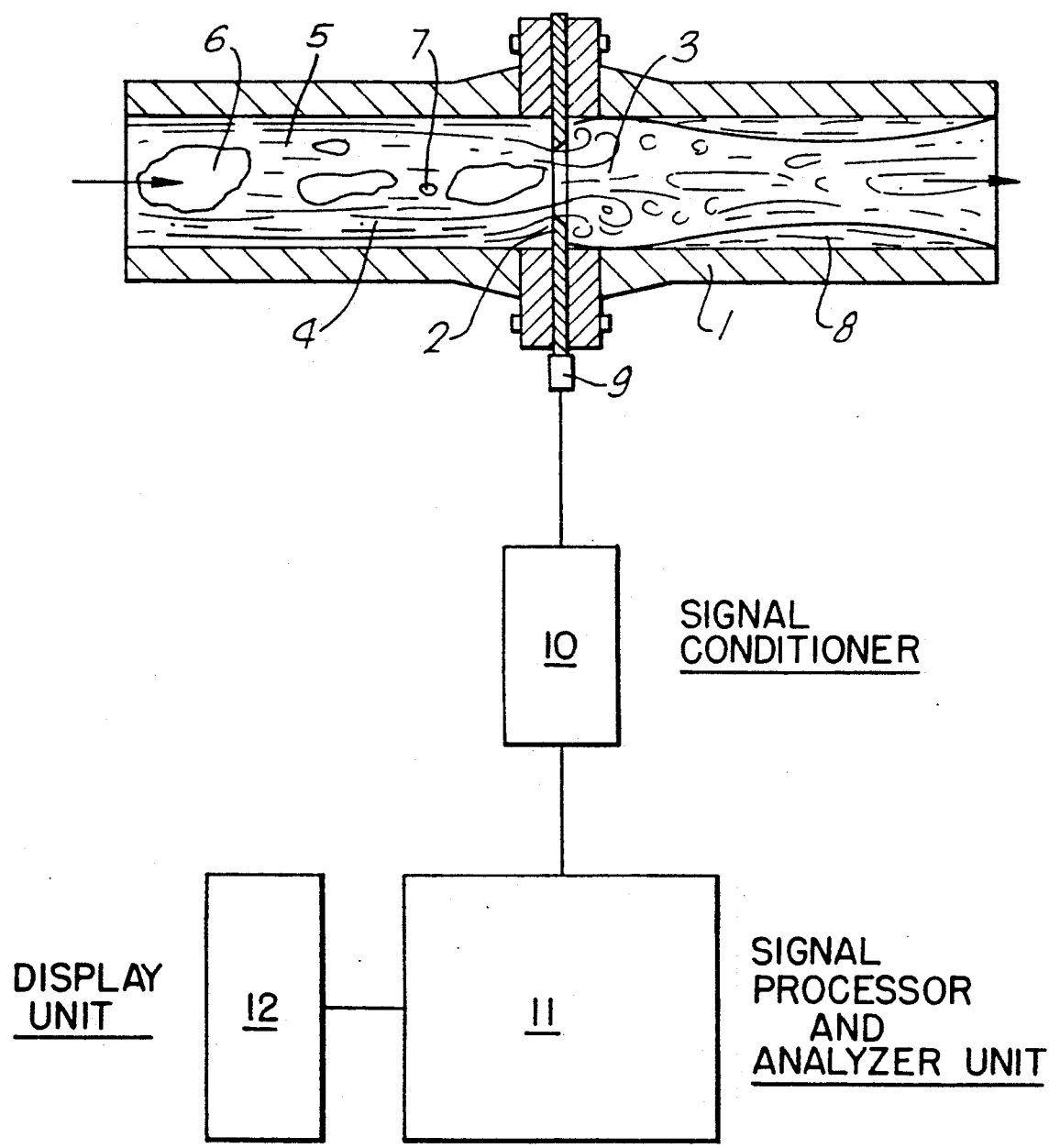
FIG. 1 illustrates a transport system with a turbulence/cavitation-causing constriction means.

FIG. 1 shows a simple basic circuit diagram of a transport system 1, e.g. a turbulence/cavitation causing device 2 such as an orifice plate in a pipeline which will cause strong turbulence/cavitation 3 in a flowing medium 4 that may consist of liquids 5, gas pockets 6, and particles 7. In the pipeline there may be precipitations in the form of, e.g. hydrate formations 8. An acoustic sensor means 9 (e.g. an accelerometer) is coupled with device 2, and signals picked up by sensor means 9 converting the acoustic signal to an electrical signal and transmitted to a signal conditioner 10, from the latter to a signal processor and analyzer unit 11, and then to a display 12.

Figure 2:
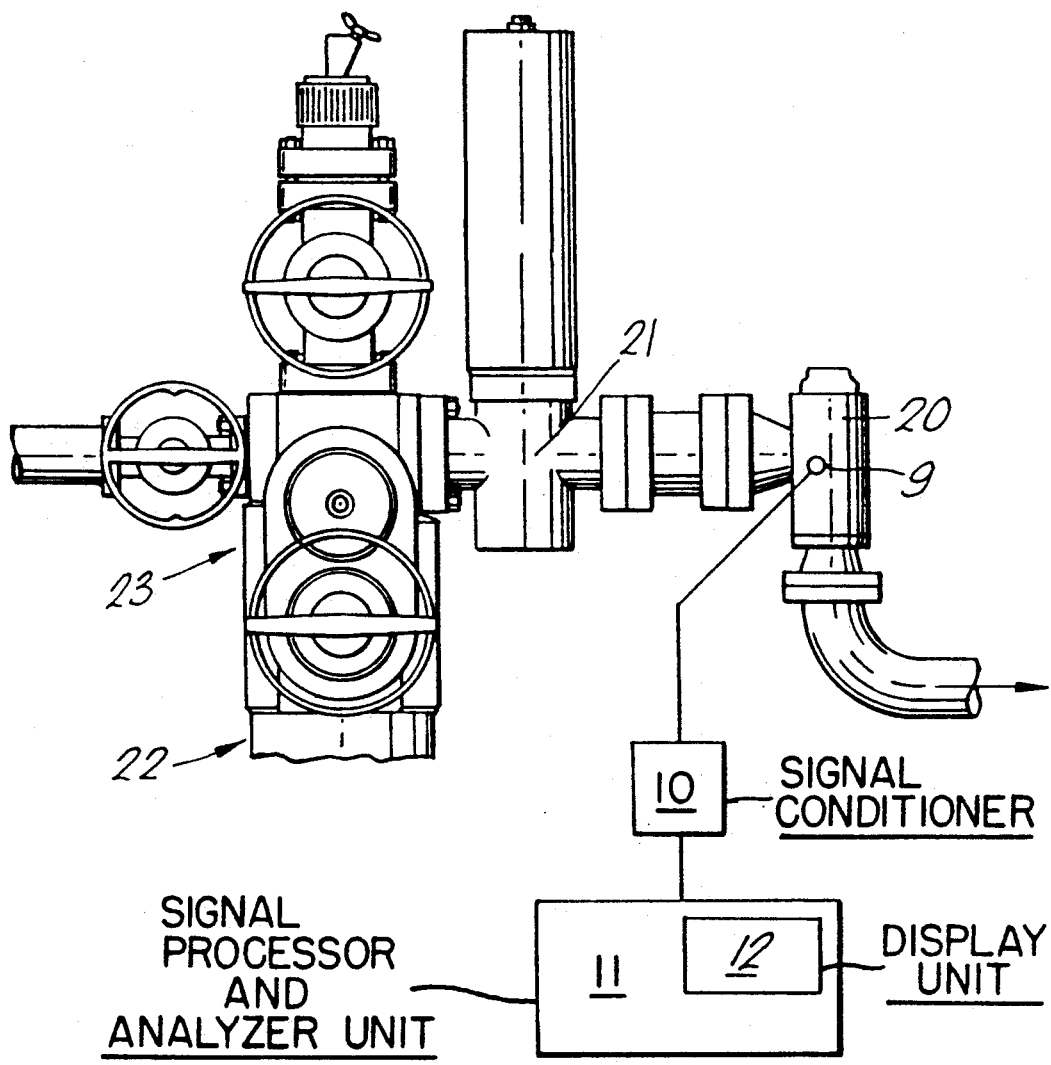
FIG. 2 illustrates utilization of a choke valve as a turbulence/cavitation-causing means in connection with a christmas tree for a production well.

FIG. 2 shows a typical utilization in connection with a choke valve 20 which is connected after a wing valve 21, which is, in turn, connected with a production well 22 by the aid of a standard christmas tree 23. The acoustic sensor means 9 is attached to choke valve 20.

Figure 3:
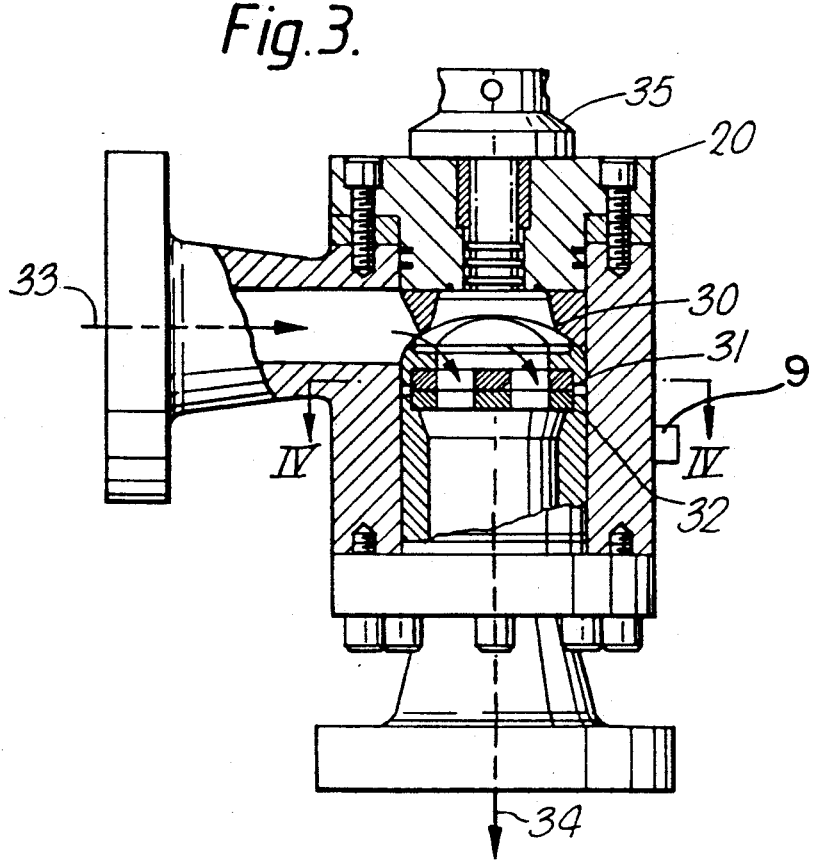
FIG. 3 illustrates a typical choke valve.

FIG. 3 shows a sectional view of an embodiment of a typical choke valve 20. Choking means 30 is centrally arranged between inlet 33 and outlet 34 and is adjustable by the aid of a drive means 35. The choking means comprises two mutually rotatable disks 31, 32, which are provided with holes 40, 41, and 42, 43, respectively.

Figure 4A:
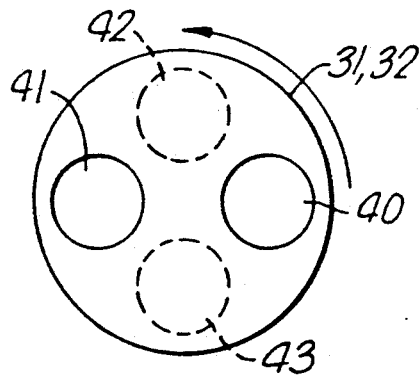
FIG. 4 illustrates a section III—III through choking means in a choke valve in three different states of operation.
Figure 4B:
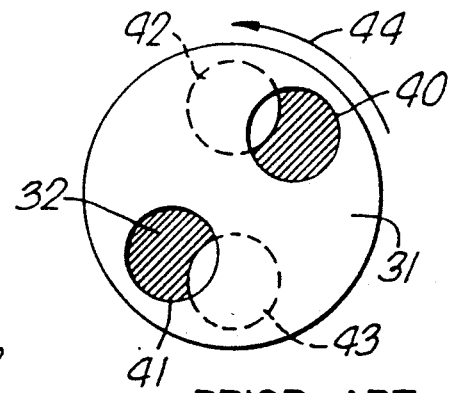
Figure 4C:
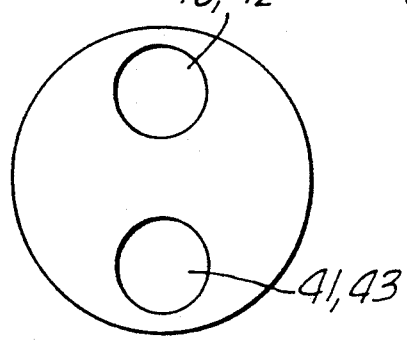

FIGS. 4a–c show choking means 30 in three different states, completely closed (FIG. 4a), in an intermediate position (FIG. 4b), and fully open (FIG. 4c). Upper disk 31 is in the shown embodiment provided with two openings 40, 41, and the lower disk is correspondingly, provided with two openings 42, 43. As shown in FIGS. 4a–c, the lower disk 32 may be stationary, whereas the uppermost disk 31 is rotatable, e.g. anticlockwise, as indicated by arrow 44.

Figure 5:
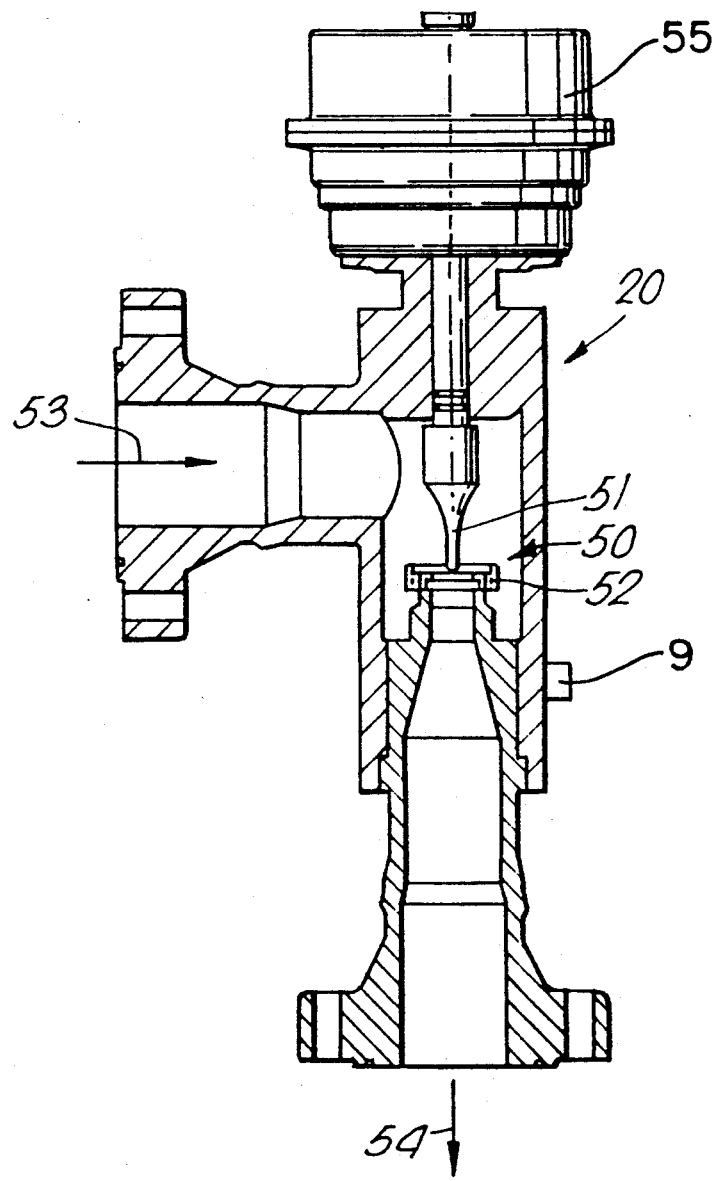
FIG. 5 shows another kind of a choke valve.

FIG. 5 shows that choke valve 20 could also have a different constriction means 50 in the shape of a cone 51 which is positioned in relation to a centrally provided valve seat 52, and which forms an adjustable constriction between inlet 53 and outlet 54. Adjustment is effected by the aid of a driving means 55 moving cone 51 axially relative to the seat valve.

Figure 6:
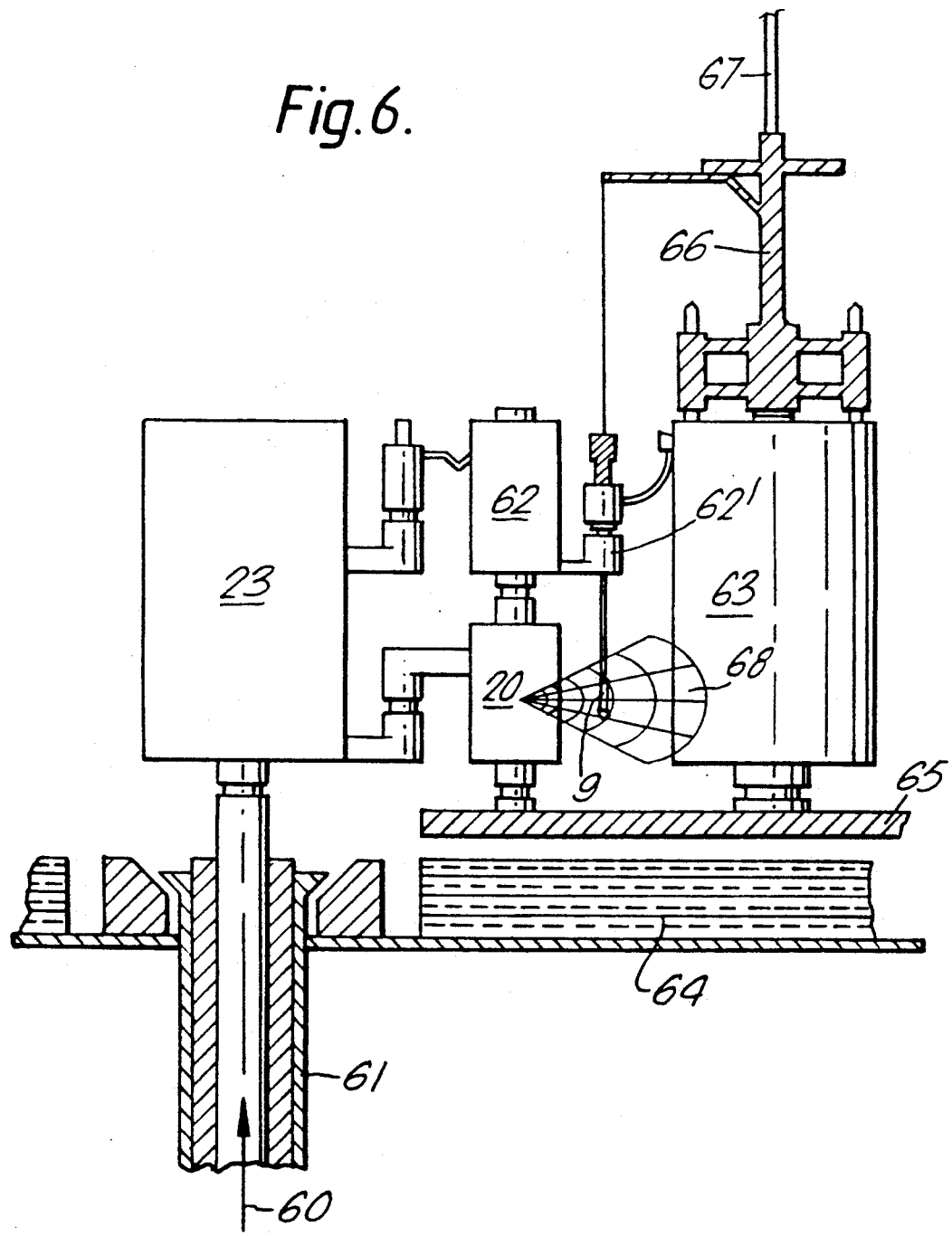
FIG. 6 illustrates the present invention in connection with a subsea structure.

FIG. 6 shows a typical subsea utilization of the invention with well flow 60 being conducted from production well 61, via a christmas tree 23, and a coupling and control unit 62 to choke valve 20. Reference number 63 designates the main control unit of the subsea structure, 64 designates a bottom frame, 65 a manifold, 66 a connecting module, and 67 a cable to the surface. Sensor means 9 is connected with connecting module 66, and when the latter is lowered towards main control unit 63, sensor means 9 may be guided downwards, e.g. through projecting member 62' of unit 62 to be positioned in the zone of acoustic signals 68 from choke valve 20.

Figure 7:
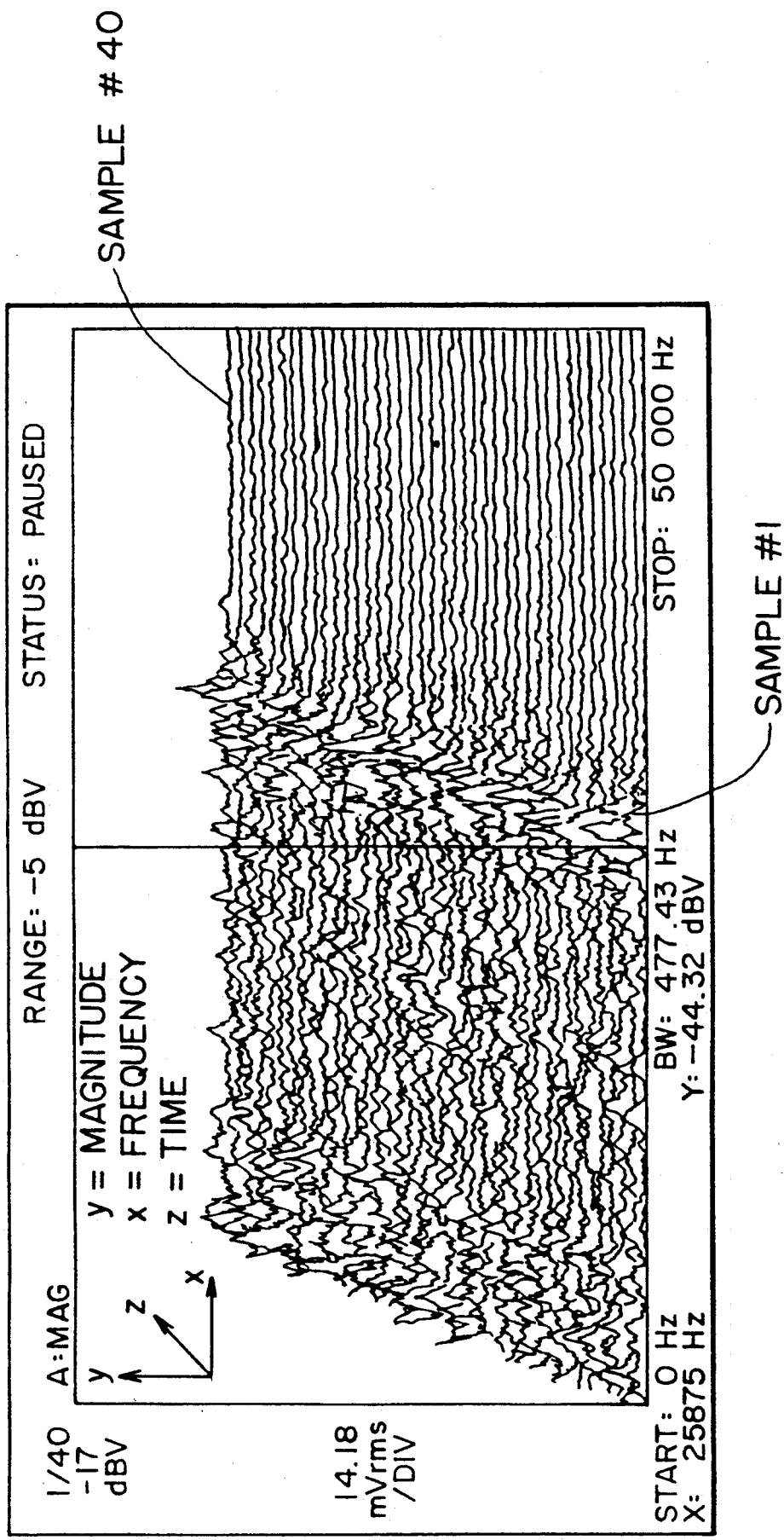
FIG. 7 shows a three-dimensional frequency spectrum picked up from a control valve of a typical oil producing well.

FIG. 7 shows an example of a three-dimensional diagram of the acoustic signal spectrum (FFT-analysis) recorded from a control valve which is in connection with a well mainly producing oil with a small portion of gas appearing in a pulsating manner in the shape of small gas slugs. Characteristically, the signal spectrum of this kind of well has a narrower bandwidth than what is typical of a gas producing well. The bandwidth is approximately 40 kHz.

Figure 8:
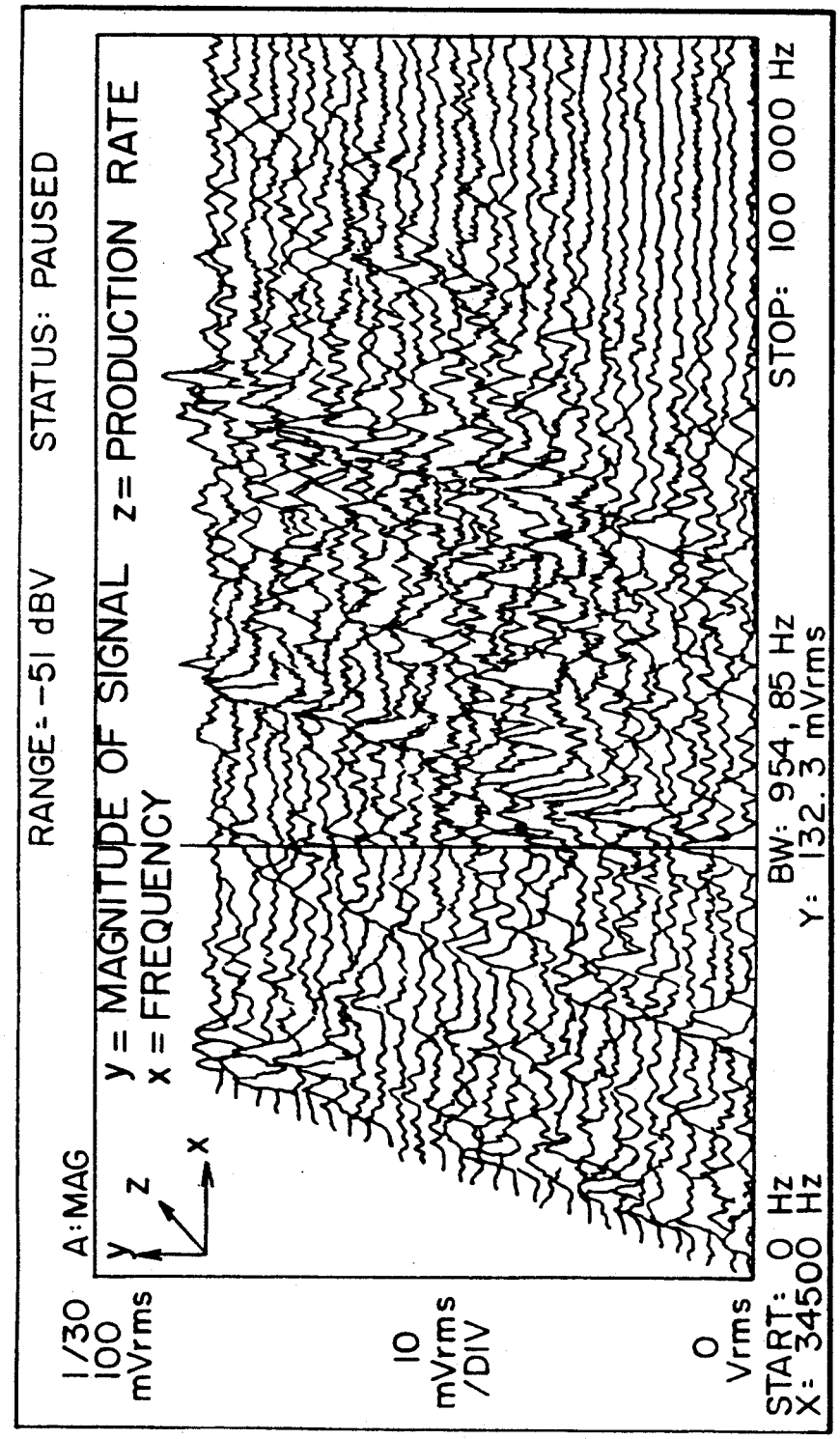
FIG. 8 shows a three-dimensional frequency spectrum picked up from a control valve of a typical gas producing well.

FIG. 8 shows essentially the same as FIG. 7, but in this case there is a typical gas well causing a much wider bandwidth, approximately 50-70 kHz.

Figure 9:
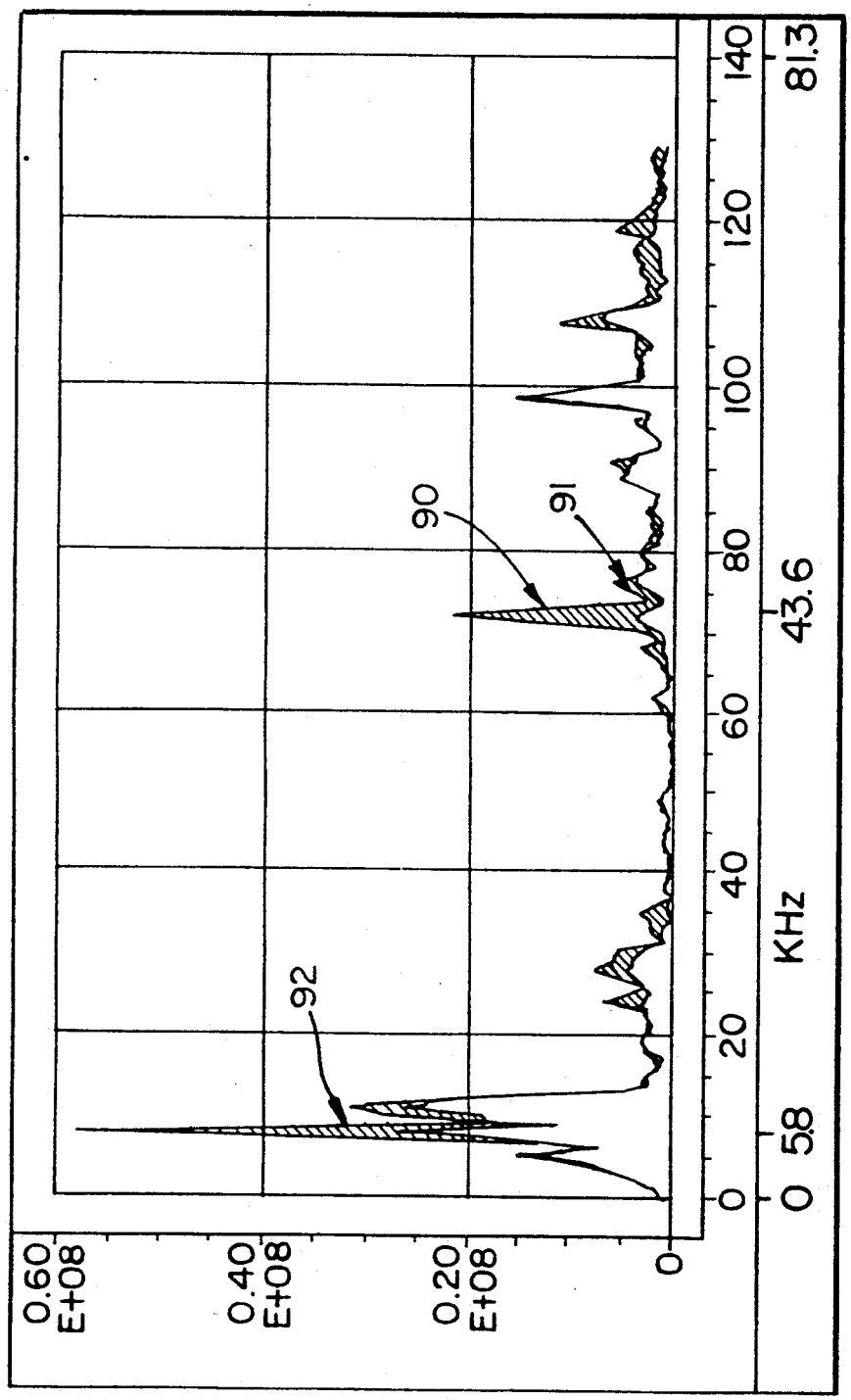
FIG. 9 shows two different power spectra with and without sand production.

FIG. 9 shows two different power spectra, with and without sand production from a control valve controlling an oil well. This illustration shows an example with characteristic features of the spectrum in cases where sand is produced and carried with the well flow through the control valve. In the FIG. 9 the horizontal axis represents resolution in the frequency range i.e. 140 corresponds to 81.3 kHz. As will appear from the diagram, the difference between a flow with and without sand production is represented by the shaded area between curves. In this example peaks 90 and 92 at 43.6 kHz, and 5.8 kHz, respectively are characteristic for sand production. The frequency at the signal level 91 is, e.g., not sensitive or characteristic of sand production.

In the low frequency region sand production is also represented by a high peak 92. For the rest, the spectra are relatively coincident. The spectra, furthermore, besides information on sand, also comprise information on a series of other flow parameters, as mentioned above. Details which are not as characteristic as information on sand will require more extensive use of different methods of analysis as well as statistical mathematical models.

I claim:

1. A method for determining the composition and flow conditions of a medium flowing through a transport system comprising,
   a) causing acoustic energy signals to be generated and propagated by the flowing medium by
      (i) forming a structural detail through which the medium must flow,
      (ii) disposing the structural detail in the transport system to change the cross-sectional flow area of the medium in the transport system at the structural detail,
      (iii) forming the structural detail to create turbulence and/or cavitation in the medium when the medium passes through the structural detail, thereby causing acoustic energy signals to be generated and propagated in the structural detail,
   b) detecting broad band acoustic energy signals generated and propagated in the structural detail, including converting the detected acoustic signals into corresponding electrical signals by using a broad band signal converter as an acoustic sensor to sense and convert the acoustic signals,
   c) locating the acoustic sensor outside the transport system,
   d) conditioning the electrical signals, and
   e) processing and analyzing the electrical signals through signal spectrum analysis to provide interpretable information on composition and flow condition parameters related to the medium passing through the structural detail.

2. The method according to claim 1 including locating the acoustic sensor away from the transport system and using water as a coupling medium to acoustically couple the structural detail to the acoustic sensor.

3. The method according to claim 1 including locating the acoustic sensor on an exterior portion of the transport system to acoustically couple the structural detail to the acoustic sensor.

4. The method according to claim 1 wherein the flow condition parameters are selected from the group consisting of flow velocity, composition of liquids, gas/liquid ratio (GOR), slug formation and presence of solids.

5. The method according to claim 1 wherein the step of forming the structural detail includes providing an abrupt constriction in the transport system at the structural detail to create an abrupt pressure drop in the medium during its passage between the upstream and downstream sides of the structural detail thereby causing turbulence and/or cavitation at the structural detail, and the step of detecting includes acoustically detecting the resulting turbulence and/or cavitation.

6. The method according to claim 5 including making all or part of the flowing medium reach a critical velocity through the structural detail with a corresponding output of acoustic energy signals.

7. The method according to claim 1 including deriving information on wear and erosion of the structural detail from the acoustic energy signals generated and propagated in the structural detail.

8. The method according to claim 1 including deriving information on the buildup of particles from the flowing medium, which are downstream of the structural detail, from the acoustic energy signals generated and propagated in the structural detail.

9. The method according to claim 1 including interpreting the acoustic signals generated at the structural detail to provide information on the accumulation of sediments or other precipitants on the interior of the structural detail or pipeline which causes a change in the state of turbulence and/or cavitation in the medium when the medium passes through the structural detail.

10. The method according to claim 1 including deriving information on the influence of the structural detail on the change of flow of the medium through the structural detail from the acoustic energy signals generated and propagated in the structural detail.

11. The method according to claim 1 wherein the step of detecting includes surrounding at least a portion of the acoustic sensor and the transport medium at the structural detail with water and using such water as a coupling medium to acoustically connect or couple the acoustic sensor with the structural detail.

12. The method according to claim 1 wherein the step of converting includes converting the acoustic signals into optical signals and then converting the optical signals into electrical signals through the acoustic sensor, and providing a display of the processed and analyzed signals.

13. The method according to claim 1 wherein the step of forming the structural detail includes the use of a flow control valve when the medium flows from a production well.

14. The method according to claim 1 including using subsea water as a coupling medium between the structural detail and the sensor when the transport system is a subsea production system, and wherein a relatively small amount of water surrounding the subsea production system is used as the coupling medium.

15. The method according to claim 1 wherein the step of detecting includes projecting the sensor from the transport system in a subsea production system such that the protruding sensor is within a signal zone of the acoustical signal emitted by the structural detail.

16. The method according to claim 1 including using an adjustable valve as the structural detail such that a change of information signal from the acoustic sensor relates to a change of the valve position.

* * * * *